US012797443B2

(12) United States Patent
Devary

(10) Patent No.: US 12,797,443 B2
(45) Date of Patent: Nov. 17, 2026

(54) POLYPEPTIDES FOR USE IN THE TREATMENT AND PREVENTION OF NEURODEGENERATIVE DISEASES

(71) Applicant: IMMUNE SYSTEM KEY LTD., Jerusalem (IL)

(72) Inventor: Yoram Devary, Jerusalem (IL)

(73) Assignee: IMMUNE SYSTEM KEY LTD., Jerusalem (IL)

( * ) Notice: Subject to any disclaimer, the term of this patent is extended or adjusted under 35 U.S.C. 154(b) by 696 days.

(21) Appl. No.: 18/251,652

(22) PCT Filed: Nov. 2, 2021

(86) PCT No.: PCT/IL2021/051297

§ 371 (c)(1),
(2) Date: May 3, 2023

(87) PCT Pub. No.: WO2022/097136

PCT Pub. Date: May 12, 2022

(65) Prior Publication Data

US 2024/0009277 A1 Jan. 11, 2024

Related U.S. Application Data

(60) Provisional application No. 63/109,484, filed on Nov. 4, 2020.

(51) Int. Cl.

| | |
|---|---|
| ***A61K 38/00*** | (2006.01) |
| ***A61K 38/22*** | (2006.01) |
| ***A61K 45/06*** | (2006.01) |
| ***A61P 25/28*** | (2006.01) |

(52) U.S. Cl.

CPC .............. *A61K 38/22* (2013.01); *A61K 45/06* (2013.01); *A61P 25/28* (2018.01)

(58) Field of Classification Search

CPC ........ A61K 38/22; A61K 45/06; A61K 38/10; A61P 25/28; C07K 7/08

See application file for complete search history.

(56) References Cited

FOREIGN PATENT DOCUMENTS

| | | | |
|---|---|---|---|
| EP | 3272752 | A1 | 1/2018 |
| EP | 2958583 | B1 | 4/2018 |
| JP | 2018512413 | A | 5/2018 |
| WO | 2006046239 | A2 | 5/2006 |
| WO | 2007091240 | A2 | 8/2007 |
| WO | 2007122622 | A1 | 11/2007 |
| WO | 2008075349 | A1 | 6/2008 |
| WO | 2015083167 | A1 | 6/2015 |
| WO | 2017134668 | A1 | 8/2017 |

OTHER PUBLICATIONS

Cleveland Clinic: Neurological Disorders: What They Are, Symptoms & Types; https://my.clevelandclinic.org/health/diseases/neurological-disorders, last visited Mar. 7, 2026.*

Imam et al. The Global Neurodegeneration Proteomics Consortium: biomarker and drug target discovery for common neurodegenerative diseases and aging. Nature Medicine, vol. 31, Aug. 2025, p. 2556-2566.*

Benatar M, Goutman SA, Staats KA, et al. A roadmap to ALS prevention: strategies and priorities Journal of Neurology, Neurosurgery & Psychiatry 2023;94:399-402.*

Wang et al. Therapeutic peptides: current applications and future directions, Signal Transduction and Targeted Therapy vol. 7, Article No. 48. 2022.*

Stemmer, Salomon M., et al. "A phase I clinical trial of dTCApFs, a derivative of a novel human hormone peptide, for the treatment of advanced/metastatic solid tumors." Molecular and clinical oncology 8.1 (2017): 22-29. Nov. 15, 2017 (Nov. 15, 2017).*

Couvineau et al. Frontiers in endocrinology, Sep. 2018, vol. 9, No. 573.*

Sandler, U. et al., 2010, A Novel Human Hormone-peptide NEROFE Selectively Induces Apoptosis in Cancer Cells through the T1/ST2 Receptor, Recent advances in clinical medicine, ISSN: 1790-5125.

Sandler, U. et al., 2010, NEROFE™—A novel human hormone-peptide with anti-cancer activity, J Experimental Therapeutics and Oncology 8:327-339.

Stemmer et al., 2017, A phase I clinical trial of dTCApFs, a derivative of a novel human hormone peptide, for the treatment of advanced/metastatic solid tumors, Molecular and Clinical Oncology 8.1.

Ohana et al, Mol Clin Oncol, 2017, vol. 7, pp. 991-999.

* cited by examiner

*Primary Examiner* — Jeanette M Lieb

(74) *Attorney, Agent, or Firm* — FISHERBROYLES, LLP; Roger L. Browdy

(57) ABSTRACT

The present disclosure provides methods, compositions and kits for use in preventing, treating, ameliorating or delaying the onset of at least one of a neurodegenerative disease, cognitive decline and any conditions or symptoms associated therewith as well as for improving at least one of cognitive function, short term memory, long term memory, learning function, glucose metabolism and glucose transport.

16 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: synthetic peptide termed "dTCApFs"
<220> FEATURE:
<221> NAME/KEY: MISC_FEATURE
<222> LOCATION: (1)..(1)
<223> OTHER INFORMATION: Xaa is equal to D-Trp
<220> FEATURE:
<221> NAME/KEY: MISC_FEATURE
<222> LOCATION: (2)..(2)
<223> OTHER INFORMATION: Xaa is equal to D-Trp
<220> FEATURE:
<221> NAME/KEY: MISC_FEATURE
<222> LOCATION: (3)..(3)
<223> OTHER INFORMATION: Xaa is equal to D-Thr
<220> FEATURE:
<221> NAME/KEY: MISC_FEATURE
<222> LOCATION: (4)..(4)
<223> OTHER INFORMATION: Xaa is equal to D-Phe
<220> FEATURE:
<221> NAME/KEY: MISC_FEATURE
<222> LOCATION: (5)..(5)
<223> OTHER INFORMATION: Xaa is equal to D-Phe
```

-continued

```
<220> FEATURE:
<221> NAME/KEY: MISC_FEATURE
<222> LOCATION: (6)..(6)
<223> OTHER INFORMATION: Xaa is equal to D-Leu
<220> FEATURE:
<221> NAME/KEY: MISC_FEATURE
<222> LOCATION: (7)..(7)
<223> OTHER INFORMATION: Xaa is equal to D-Pro
<220> FEATURE:
<221> NAME/KEY: MISC_FEATURE
<222> LOCATION: (8)..(8)
<223> OTHER INFORMATION: Xaa is equal to D-Ser
<220> FEATURE:
<221> NAME/KEY: MISC_FEATURE
<222> LOCATION: (9)..(9)
<223> OTHER INFORMATION: Xaa is equal to D-Thr
<220> FEATURE:
<221> NAME/KEY: MISC_FEATURE
<222> LOCATION: (10)..(10)
<223> OTHER INFORMATION: Xaa is equal to D-Leu
<220> FEATURE:
<221> NAME/KEY: MISC_FEATURE
<222> LOCATION: (11)..(11)
<223> OTHER INFORMATION: Xaa is equal to D-Trp
<220> FEATURE:
<221> NAME/KEY: MISC_FEATURE
<222> LOCATION: (12)..(12)
<223> OTHER INFORMATION: Xaa is equal to D-Glu
<220> FEATURE:
<221> NAME/KEY: MISC_FEATURE
<222> LOCATION: (13)..(13)
<223> OTHER INFORMATION: Xaa is equal to D-Arg
<220> FEATURE:
<221> NAME/KEY: MISC_FEATURE
<222> LOCATION: (14)..(14)
<223> OTHER INFORMATION: Xaa is equal to D-Lys

<400> SEQUENCE: 1

Xaa Xaa Xaa Xaa Xaa Xaa Xaa Xaa Xaa Xaa Xaa Xaa Xaa Xaa
1               5                   10


<210> SEQ ID NO 2
<211> LENGTH: 14
<212> TYPE: PRT
<213> ORGANISM: Artificial Sequence
<220> FEATURE:
<223> OTHER INFORMATION: L-amino acid peptide of "dTCApFs"

<400> SEQUENCE: 2

Trp Trp Thr Phe Phe Leu Pro Ser Thr Leu Trp Glu Arg Lys
1               5                   10
```

POLYPEPTIDES FOR USE IN THE TREATMENT AND PREVENTION OF NEURODEGENERATIVE DISEASES

TECHNOLOGICAL FIELD

The present disclosure generally relates to polypeptides useful in the treatment, prevention and diagnosis of neurodegenerative diseases and conditions.

BACKGROUND ART

References considered to be relevant as background to the presently disclosed subject matter are listed below:

[1] WO 2006/046239.
[2] WO 20 07/122622.
[3] WO 2007/091240.
[4] WO 2008/075349.
[5] Sandler, U. et al., 2010, Recent advances in clinical medicine, ISSN: 1790-5125.
[6] Sandler, U. et al., 2010, J Experimental Therapeutics and Oncology 8:327-339.
[7] WO 2015/083167.
[8] WO 2017/134668.

Acknowledgement of the above references herein is not to be inferred as meaning that these are in any way relevant to the patentability of the presently disclosed subject matter.

BACKGROUND OF THE INVENTION

Neurodegenerative diseases affect millions of people worldwide. Alzheimer's disease and Parkinson's disease are the most common neurodegenerative diseases. According to the National Institute of Environmental Health Sciences (NIH), in 2016, an estimated 5.4 million Americans were living with Alzheimer's disease.

Neurodegenerative diseases occur when nerve cells in the brain or peripheral nervous system lose function over time and ultimately die. While treatments may relieve some of the physical or mental symptoms associated with neurodegenerative diseases, there is currently no way to slow down disease progression and no known cures.

It is widely acceptable that the development of neurodegenerative diseases commences 10-20 years prior to their clinical manifestation. Although molecular mechanisms behind various neurodegenerative diseases are different, many processes, for example neurite retraction, dysfunction and destruction of synapses and ultimately neuronal death, are characteristic of neurodegeneration in general.

Furthermore, therapy in late stages of neurodegenerative diseases appears to be ineffective, most likely due to massive neuronal death, thus highlighting the importance of early detection and preventive measures.

A peptide termed "T101" was previously identified, as reported in the publication WO 2006/046239 (1). This peptide and derivatives thereof were suggested, inter alia, for treatment of cancer. Treatment of cancer by using T101 was also suggested in the publication WO 2007/122622 (2), which demonstrates, among others, the effect of T101 on the development of various types of tumors. The peptide T101 was also described in the publication WO 2007/091240 (3) which relates, among others, to treatment of immunological diseases and in the publication WO 2008/075349 (4) as well as in the publications by Sandler et al. (5 and 6), relating to treating or preventing a disease involving a cell having T1/ST2 receptor.

In addition, an additional peptide derivative of T101, in which all of the amino acid residues are in their D configuration, has been previously reported to decrease the secretion of proteins that are known to be associated with cancer metastasis and to directly inhibit migration of cancer cells in vitro (7). This peptide derivative was further suggested for use in combination with additional anti-cancer agents, for the treatment of cancer (8).

SUMMARY OF THE INVENTION

In a first of its aspects, the present disclosure provides a method for preventing, treating, ameliorating or delaying the onset of at least one of a neurodegenerative disease, cognitive decline and any conditions or symptoms associated therewith in a subject in need thereof, comprising administering to said subject an effective amount of an isolated polypeptide comprising the amino acid sequence of SEQ ID NO: 1 or a functional fragment or derivative of the isolated polypeptide or a salt thereof.

In a second of its aspects, the present disclosure further provides a method for improving at least one of cognitive function, short term memory, long term memory, learning function, glucose metabolism and glucose transport in a subject in need thereof, comprising administering to said subject an effective amount of an isolated polypeptide comprising the amino acid sequence of SEQ ID NO: 1 or a functional fragment or derivative of the isolated polypeptide or a salt thereof.

In a third of its aspects, the present disclosure provides a combination therapy comprising an isolated peptide comprising the amino acid sequence denoted by SEQ ID NO. 1 or a functional derivative thereof or a pharmaceutically acceptable salt of said isolated peptide and at least one additional therapeutic agent for use in a method of preventing, treating, ameliorating or delaying the onset of at least one of a neurodegenerative disease, cognitive decline and any conditions or symptoms associated therewith in a subject in need thereof.

In a fourth of its aspects, the present disclosure provides a combination therapy comprising an isolated peptide comprising the amino acid sequence denoted by SEQ ID NO. 1 or a functional derivative thereof or a pharmaceutically acceptable salt of said isolated peptide and at least one additional therapeutic agent for use in improving at least one of cognitive function, short term memory, long term memory, learning function, glucose metabolism and glucose transport in a subject in need thereof.

In yet a fifth of its aspects, the present disclosure provides an isolated polypeptide comprising the amino acid sequence of SEQ ID NO: 1 or a functional fragment or derivative of said isolated polypeptide or a salt thereof for use in a method for preventing, treating, ameliorating or delaying the onset of at least one of a neurodegenerative disease, cognitive decline and any conditions or symptoms associated therewith in a subject in need thereof, said method comprises administering to said subject an effective amount of said isolated polypeptide, a functional fragment or derivative of said isolated polypeptide or of a salt thereof.

By another sixth of its aspects, the present disclosure further provides an isolated polypeptide comprising the amino acid sequence of SEQ ID NO: 1 or a functional fragment or derivative of said isolated peptide or a salt thereof for use in a method for improving at least one of cognitive function, short term memory, long term memory, learning function, glucose metabolism and glucose transport in a subject in need thereof, said method comprises administering to said subject an effective amount of said isolated polypeptide, a functional fragment or derivative of said isolated peptide or of a salt thereof.

Still further another in a seventh of its aspects, the present disclosure provides a pharmaceutical composition comprising an isolated polypeptide comprising the amino acid sequence of SEQ ID NO: 1 or a functional fragment or derivative of said isolated polypeptide or a salt thereof, and at least one pharmaceutically acceptable excipient, carrier or diluent, for use in a method for preventing, treating, ameliorating or delaying the onset of at least one of a neurodegenerative disease, cognitive decline and any conditions or symptoms associated therewith in a subject in need thereof.

By a further eighth of its aspects, the present disclosure provides a pharmaceutical composition comprising an isolated polypeptide comprising the amino acid sequence of SEQ ID NO: 1 or a functional fragment or derivative of said isolated polypeptide or a salt thereof, and at least one pharmaceutically acceptable excipient, carrier or diluent, for use in a method for improving at least one of cognitive function, short term memory, long term memory, learning function, glucose metabolism and glucose transport in a subject in need thereof.

In the ninth of its aspects, the present disclosure further provides a kit comprising:

(a) an isolated polypeptide comprising the amino acid sequence of SEQ ID NO: 1 or a functional fragment or derivative of the isolated polypeptide or a salt thereof; and optionally (b) at least one pharmaceutically acceptable excipient, carrier or diluent;

for use in a method for at least one of preventing, treating, ameliorating or delaying the onset of at least one of a neurodegenerative disease, cognitive decline and any conditions or symptoms associated therewith in a subject in need thereof.

Still further by a tenth of its aspects, the present disclosure provides a kit comprising:

(a) an isolated polypeptide comprising the amino acid sequence of SEQ ID NO: 1 or a functional fragment or derivative of the isolated polypeptide or a salt thereof; and optionally (b) at least one pharmaceutically acceptable excipient, carrier or diluent;

for use in a method for improving at least one of cognitive function, short term memory, long term memory, learning function, glucose metabolism and glucose transport in a subject in need thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 6A-FIG. 5C show the effect of a polypeptide having the amino acid sequence of dTCApFs though in all L amino acid configuration (indicated "NF") on the expression levels of the proteins XBP1 (FIG. 6A), p53 (FIG. 6B) and GLUT1 (FIG. 6C) in human neuroblastoma cells cells (SHSY5Y cells).

DETAILED DESCRIPTION OF EMBODIMENTS

Figure 1A:
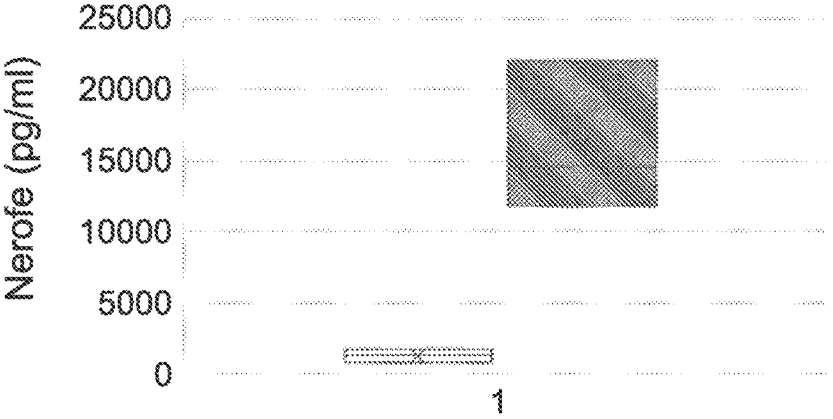
FIG. 1A-FIG. 1B are bar graphs showing in FIG. 1A the level of the polypeptide dTCApFs (also termed herein "Nerofe", which is an all D amino acid polypeptide) in a brain faction of mice injected i.p. with dTCApFs (right bar) as compared to the level of the polypeptide in the brain of mice injected with 5% mannitol solution (left bar) and in FIG. 1B the level of a polypeptide having the sequence of dTCApFs though in all L amino acid residue configuration in a brain faction of mice injected i.p. with dTCApFs in all L amino acid residue configuration (right bar) as compared to the level of the polypeptide in the brain of mice injected with 5% mannitol solution (left bar).

The present disclosure is based on the surprising neuroprotective and therapeutic effects shown for the polypeptide dTCApFs, also termed herein "Nerofe", which has the amino acid sequence WWTFFLPSTLWERK in an all-D configuration (as denoted by SEQ ID NO: 1).

As shown in the Examples below, a good penetration ability of the BBB in mice was demonstrated for the polypeptide dTCApFs.

In addition, SH-SY5Y cells, which are often used as a model of neuronal function and differentiation (for example as means or studying Parkinson's disease) were used as a cellular model to study the effect of dTCApFs. In this model, dTCApFs was shown to have a protective effect from hydrogen peroxide insults, in a dose dependent manner, as detailed in the appended Examples. It is of note that the protective effect on oxidative stress was better for the polypeptide dTCApFs in which all amino acid residues are all in the D configuration than for the corresponding polypeptide in which all the amino acid residues are in the L configuration.

Furthermore, when the effect of dTCApFs on gene expression in SH-SY5Y cells was examined, up regulation of the Superoxide dismutase 1 (SOD1) gene expression was observed. Since the gene product of SOD1 assists in cell protection against oxidative stress, which is one of the manifestations of the development of neurodegenerative diseases and disorders, the above result provides further evidence to a protective effect to the cells by dTCApFs.

The effect of dTCApFs on expression of glucose transporters in human neurons was also examined by incubating SH-SY5Y cells in the presence of increasing doses of dTCApFs. As detailed below, the levels of Glucose Transporter 1 (GLUT1) and Glucose Transporter 3 (GLUT3) proteins were increased with the increase in dTCApFs doses, suggesting a further beneficial protective effect of the polypeptide on brain glucose metabolism and transportation, which are dramatically decreased in neurological disorders.

The effect of dTCApFs on expression of the XBP1 gene was further tested in SH-SY5Y cells. XBP1 is an important transcription factor in human brain to which a beneficial effect on memory and cognitive capabilities is attributed. Surprisingly, expression of the XBP1 protein was highly induced in the presence of the dTCApFs polypeptide.

Furthermore, incubation of the above cells in the presence of the dTCApFs polypeptide completely downregulated p53 expression in these cells. Lowering the expression level of p53 is considered to be a beneficial effect, since it leads to an increase in glucose metabolism.

Therefore, by a first aspect thereof, the present disclosure provides a method for preventing, treating, ameliorating or delaying the onset of at least one of a neurodegenerative disease, cognitive decline and any conditions or symptoms associated therewith in a subject in need thereof, comprising administering to said subject an effective amount of an isolated polypeptide comprising the amino acid sequence of SEQ ID NO: 1 or a functional fragment or derivative of the isolated polypeptide or a salt thereof.

In some embodiments, the method according to the present disclosure results in amelioration or reduction of at least one condition or symptom associated with at least one of a neurodegenerative disease and cognitive decline in a subject in need thereof.

In various embodiments the condition or symptom according to the present disclosure is at least one of anxiety, short term memory impairment, long term memory impairment, impaired cognitive function, impaired learning function, impaired glucose metabolism, oxidative stress or any combination thereof.

In some embodiments, the method according to the present disclosure results in improvement of at least one of cognitive function, short term memory, long term memory, learning function and glucose metabolism and glucose transport in a subject in need thereof.

In some specific embodiments, the present disclosure provides a method for preventing or delaying the onset of at least one of a neurodegenerative disease, cognitive decline and any conditions or symptoms associated therewith in a subject in need thereof, comprising administering to said subject an effective amount of an isolated polypeptide comprising the amino acid sequence of SEQ ID NO: 1 or a functional fragment or derivative of the isolated polypeptide or a salt thereof.

As it can be appreciated, the term "neurodegenerative disease" as used herein refers to a heterogeneous group of disorders that are characterized by the progressive degeneration of the structure and function of the central nervous system or the peripheral nervous system.

Any known neurodegenerative disease is encompassed by the present disclosure. For example, but not limited to, Alzheimer's disease, Parkinson's disease, dementia (also known as "major neurocognitive disorder" and "mild neurocognitive disorder"), Mild Cognitive Impairment (MCI), Parkinson's disease with MCI, Huntington's disease, Lewy body disease, Amyotrophic lateral sclerosis (ALS), Prion disease, Motor neuron disease (MND), Spinocerebellar ataxia (SCA), Spinal muscular atrophy (SMA), Friedreich's Ataxia or a disorder associated with protein misfolding, memory decline and anxiety, to name but few.

Mental disorders with neurodegenerative basis are also encompassed under the term neurodegenerative disease as herein defined, for example but not limited to, bipolar disorder.

Diagnosis of a neurodegenerative disease may be performed by a skilled physician according to methods well known in the art.

In the above and other embodiments the neurodegenerative disease according to the present disclosure is Alzheimer's disease, Parkinson's disease, Dementia, a disorder associated with protein misfolding, cognitive decline, Mild Cognitive Impairment (MCI), Parkinson's disease with MCI, Huntington's disease, Lewy body disease, Amyotrophic lateral sclerosis (ALS), Prion disease, Motor neuron disease (MND), Spinocerebellar ataxia (SCA), Spinal muscular atrophy (SMA), Friedreich's Ataxia, multiple sclerosis, Idiopathic Intracranial Hypertension, Cranial neuropathies, Trigeminal neuralgia, frontotemporal dementias (FTD), Senile Dementia (Dementia NOS), Motor Neuron Disease, or bipolar disorder.

In particular embodiments, the neurodegenerative disease according to the present disclosure is Alzheimer's disease.

Alzheimer's disease (AD) as known in the art relates to a progressive neurodegenerative disease that is manifested, among others, in damage and eventually destruction of brain cells, leading to memory loss and changes in cognitive and other brain functions. More specifically, AD, refers to a disorder that involves deterioration of memory and other cognitive domains that leads to death within 3 to 9 years after diagnosis. The principal risk factor for Alzheimer's disease is age. The incidence of the disease doubles every 5 years after 65 years of age, however, up to 5% of people with the disease have early onset AD (also known as younger-onset) that may appear at 40 or 50 years of age.

AD is a progressive disease, where dementia symptoms gradually worsen over several years. In its early stages, memory loss is mild, but with late-stage AD, individuals lose the ability to carry on a conversation and respond to their environment. Those with AD live an average of eight years after their symptoms become noticeable to others, but survival can range from four to 20 years, depending on age and other health conditions.

The most common early symptom of AD is difficulty remembering newly learned information because AD changes typically begin in the part of the brain that affects learning. As AD advances through the brain it leads to increasingly severe symptoms, including disorientation, mood and behavior changes, deepening confusion about events, time and place, unfounded suspicions about family, friends and professional caregivers, more serious memory loss and behavior changes and difficulty speaking, swallowing and walking.

Beside symptomatic treatments to temporarily slow the worsening of dementia symptoms, AD has no current cure, and the current treatments cannot stop AD from progressing.

Diagnosis of AD may be performed by a skilled physician and include physical examinations and diagnostic tests (for example a Mini-Mental State Exam (MMSE)). Early signs and symptoms of Alzheimer's include among others memory impairment, difficulty concentrating, planning or problem-solving, problems with finishing daily tasks, confusion, language problems such as word-finding problems or reduced vocabulary in speech or writing, changes in mood, such as depression or other behavior and personality changes.

It should be appreciated that the polypeptide or a functional fragment or derivative thereof, salt thereof or any pharmaceutical composition comprising the same of the present disclosure are suitable for treating any stage of AD, at any age and for any conditions and symptoms associated therewith.

In other specific embodiments, as detailed above, the methods of the present disclosure are applicable, inter alia, to Parkinson's disease or Dementia.

In particular embodiments, the neurodegenerative disease according to the present disclosure is Parkinson's disease.

As known in the art, Parkinson's disease is a progressive nervous system disorder that affects movement. Symptoms start gradually, sometimes starting with a barely noticeable tremor in just one hand. Tremors are common, but the disorder also commonly causes stiffness or slowing of movement. Parkinson's disease symptoms worsen as the condition progresses over time. Currently, no cure is available for Parkinson's disease. However, medications might significantly improve the symptoms.

Parkinson's signs and symptoms may include tremor (or shaking, usually begins in a limb), slowed movement (bradykinesia), rigid muscles, impaired posture and balance, loss of automatic movements, speech changes, writing changes.

In further particular embodiments, the neurodegenerative disease according to the present disclosure is Dementia.

It should be appreciated that the term "Dementia" is used herein in a broad sense and refers to a broad category of brain diseases that cause a long-term and often gradual decrease in the ability to think and remember, severe to the extent of affecting daily functioning. The term "dementia" also encompasses major neurocognitive disorder and mild neurocognitive disorder. Symptoms include emotional problems, difficulties with language and a decrease in motivation. A diagnosis of dementia requires a change from a person's usual mental functioning and a greater decline than one would expect due to aging and is performed by a skilled physician.

In some embodiments, the method as herein defined is for preventing, treating, ameliorating, or delaying the onset of cognitive decline.

As known in the art, by the term "cognitive decline" as used herein it is referred to a gradual deterioration of mental faculties due to a neurological and/or psychological disturbance such as Alzheimer's disease, dementia, depression, or substance abuse.

In other words, the present disclosure provides a method for preventing, treating, ameliorating or delaying the onset of cognitive decline and any conditions or symptoms associated therewith in a subject in need thereof, comprising administering to said subject an effective amount of an isolated polypeptide comprising the amino acid sequence of SEQ ID NO: 1 or a functional fragment or derivative of the isolated polypeptide or a salt thereof.

In specific embodiment the present disclosure pertains to cognitive decline which is due to Alzheimer's disease.

As detailed above, the present disclosure provides a method for preventing, treating, ameliorating, or delaying the onset of at least one of a neurodegenerative disease, cognitive decline and any conditions or symptoms associated therewith in a subject in need thereof.

The terms "treat", "treating", "treatment" as used herein mean improving or reducing one or more clinical indicia of disease activity in a subject having a disease or disorder as herein defined. Improvement or reduction in the clinical indicia of disease may be subtle or significant. The terms "disease", "disorder" or "condition" refer to a state in which there is a disturbance of normal functioning.

By the term "at least one" in the context of the "disease", "disorder" or "condition" as herein defined it is meant that a beneficial (therapeutic or prophylactic) effect may be achieved in at least one, for example 2, 3, 4, 5 or more diseases, disorders or conditions as herein defined, by administering the polypeptide, derivative or fragment thereof, salt thereof of the pharmaceutical composition comprising the same of the present disclosure.

Any condition or symptom associated with at least one of a neurodegenerative disease and cognitive decline in a subject in need thereof is encompassed by the present disclosure. Such symptoms (or conditions) generally include, but are not limited to, decline in mental abilities (for example short-term memory and long-term memory decline, impaired learning function), behavioral and psychiatric problems, lack of coordination, unsteady gait, speech changes, tremor, confusion with time or place, decreased or poor judgment, changes in mood and personality.

In some embodiments the method according to the present disclosure results in amelioration or reduction of at least one condition or symptom associated with at least one of a neurodegenerative disease and cognitive decline in a subject in need thereof.

By the term "amelioration" as used herein it is meant to reduce, alleviate, lighten, improve or relieve by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% at least one of the symptoms associated with at least one neurodegenerative disease and cognitive decline in a subject in need thereof.

The terms "ameliorating" and "reducing" are used herein interchangeably.

In specific embodiments the condition or symptom according to the present disclosure is at least one of anxiety, short term memory impairment, long term memory impairment, impaired cognitive function, impaired learning function, impaired glucose metabolism, oxidative stress or any combination thereof.

As known in the art, experiencing occasional anxiety is a normal part of life. However, people with anxiety (also referred to as "anxiety disorders") frequently have intense, excessive, and persistent worry and fear about everyday situations. Often, anxiety disorders involve repeated episodes of sudden feelings of intense anxiety and fear or terror that reach a peak within minutes (panic attacks). Examples of anxiety disorders include generalized anxiety disorder, social anxiety disorder (social phobia), specific phobias and separation anxiety disorder.

As known in the art, the term "short term memory" (also referred to as "primary" or "active memory") as used herein refers to the capacity for holding, but not manipulating, a small amount of information in mind in an active, readily available state for a short period of time. For example, short-term memory can be used to remember a phone number that has just been recited.

"Short-term memory impairment" as known in the art and as used herein refers to a situation when a person can remember incidents from 20 years ago but is fuzzy on the details of things that happened 20 minutes prior. It can cause people to forget the question they just asked or where they set their glasses down. Repetition of questions and behaviors is often a result of short-term memory impairment in dementia. There are a number of causes of short-term memory loss or impairment, some which are a result of medical conditions and others that are related to injuries or other outside influences. Short-term memory impairment is one of the earlier symptoms of for example Alzbeimer's disease.

Long-term memory (LTM) is the stage where informative knowledge is held indefinitely. It is defined in contrast to short-term and working memory, which persist for only about 18 to 30 seconds. Long-term memory loss or impairment as herein defined and as known in the art relates to a condition when a subject is experiencing trouble recalling information when he or she needs it. Long-term memory weakening is a normal part of aging.

By the term "cognitive function" as known in the art and as defined herein it is meant to relate to any mental process that involves symbolic operations, perception, memory, creation of imagery, and thinking and that encompasses awareness and capacity for judgment. "Impaired cognitive function" is when a person has trouble with cognitive function, for example as remembering, learning new things, concentrating, or making decisions that affect their everyday life. Cognitive impairment ranges from mild to severe. With mild impairment, people may begin to notice changes in cognitive functions, but still be able to do their everyday activities. Severe levels of impairment can lead to losing the ability to understand the meaning or importance of something and the ability to talk or write, resulting in the inability to live independently.

In some embodiments the impaired cognitive function includes impaired learning function. The term "impaired learning function" as herein defined means a decrease or reduction in the learning function or learning ability, which may be defined for example as involving acquisition, organization, retention, understanding or use of verbal or non-verbal information. Impaired learning function results from impairments in one or more processes related to perceiving, thinking, remembering or learning, and may also involve difficulties with organizational skills, social perception, social interaction and perspective taking.

The present disclosure encompasses, among others, the neurodegenerative disease Mild cognitive impairment (MCI), which is the stage between the expected cognitive decline of normal aging and the more serious decline of dementia. MCI is characterized by problems with memory, language, thinking or judgment.

In various embodiments the method according to the present disclosure results in improvement of at least one of cognitive function, short term memory, long term memory, learning function, glucose metabolism and glucose transport in a subject in need thereof.

Furthermore, the present disclosure provides a method for improving at least one of cognitive function, short term memory, long term memory, learning function, glucose metabolism and glucose transport in a subject in need thereof, comprising administering to said subject an effective amount of an isolated polypeptide comprising the amino acid sequence of SEQ ID NO: 1 or a functional fragment or derivative of the isolated polypeptide or a salt thereof.

By the term "improvement" as used herein it is meant any recovery, advance or enhancement by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% of at least one of cognitive function, short term memory, long term memory, learning function, glucose metabolism and glucose transport in a subject in need thereof.

By the term "preventing" it is meant to provide a "preventive treatment" or "prophylactic treatment", namely acting in a protective manner, defending against, or preventing something, especially a condition or disease as herein defined.

As known in the art, the disease, disorder, or condition as herein defined progress until they significantly impede the affected individual's quality of life. By the term "delaying the onset" in the context of the disorder, disease or condition as defined herein, it is meant any postponement, suspension, impediment or retardation of the manifestation of the disease or symptoms associated therewith as herein defined.

In other embodiments, the functional fragment or derivative of the isolated polypeptide according to the present disclosure (namely the isolated polypeptide comprising the amino acid sequence of SEQ ID NO: 1) has at least 70% identity to the amino acid sequence denoted by SEQ ID NO. 1.

In further embodiments, the isolated polypeptide according to the present disclosure consists of the amino acid sequence denoted by SEQ ID NO. 1.

In further embodiments, the isolated polypeptide according to the present disclosure is able to penetrate the Blood Brain Barrier.

In some embodiments, the method according to the present disclosure results in protection from oxidative stress in the neurons of said subject.

In some further embodiments, the peptide according to the present disclosure modulates the expression of at least one gene associated with protection from oxidative stress.

In some more specific embodiments, the at least one gene modulated by the peptide disclosed herein is any one of Superoxide dismutase 1 (SOD1), Brain-Derived Neurotrophic Factor (BDNF) and Tyrosine Hydroxylase (TH).

In some embodiments, the method according to the present disclosure method results in increasing glucose metabolism and/or transport in the neurons of said subject.

In some further embodiments, the peptide according to the present disclosure modulates the expression of at least one gene associated with glucose metabolism and/or transport.

In some more specific embodiments, the at least one gene modulated by the peptide disclosed herein is any one of GLUT1, GLUT3 and P53.

In some embodiments, the expression of the genes GLUT1 and GLUT3 is increased while the expression of the P53 gene is decreased by the peptide disclosed herein in the subject's neurons.

As detailed above the method according to the present disclosure results inter alia in improvement of glucose metabolism and glucose transport in a subject in need thereof.

By the term "glucose metabolism" (also referred to as "carbohydrate metabolism") as herein defined it is generally referred to oxidation, breakdown, and synthesis of carbohydrate in the living body's tissues. Glucose transporters are a wide group of membrane proteins that facilitate the transport of glucose across the plasma membrane, a process known inter alia as "facilitated diffusion". Since glucose is a vital source of energy for all life, these transporters are present in all phyla. Therefore, by the term "glucose transport" as herein defined it is referred to an entity associated with the transportation or transfer of carbohydrates in living organisms.

Glucose metabolism can be impaired by defects in insulin secretion from pancreatic beta cells or from defects in cellular sensitivity to insulin. It is well documented that impaired glucose metabolism or mitochondrial dysfunction is one of the major pathological changes observed in various neurodegenerative diseases including AD, Parkinson's disease (PD) or Huntington's disease (HD), thus suggesting that regulation of glucose metabolism and maintenance of mitochondrial homeostasis are critical for brain function.

By the term "oxidative stress" it is referred to an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

In humans, oxidative stress is thought to be involved in the development of various diseases, among which are attention deficit hyperactivity disorder (ADHD), cancer, Parkinson's disease, Lafora disease, Alzheimer's disease, atherosclerosis, heart failure, myocardial infarction and others.

In further embodiments, the method as herein defined comprises administering a pharmaceutical composition comprising said isolated polypeptide or a functional fragment or derivative of said isolated polypeptide or a salt thereof.

As detailed above, the present disclosure relates to methods of administering, uses of and pharmaceutical compositions comprising an isolated polypeptide comprising the amino acid sequence of SEQ ID NO: 1 or a functional fragment or derivative of the isolated polypeptide or a salt thereof based on the surprising neuroprotective and therapeutic effects shown for the polypeptide dTCApFs (also termed herein "Nerofe").

The amino acid sequence of the polypeptide dTCApFs (Nerofe) is WWTFFLPSTLWERK in a single-letter code and Trp Trp Thr Phe Phe Leu Pro Ser Thr Leu Trp Glu Arg Lys in three letter code, in which all of the amino acid residues are in their D configuration. The amino acid sequence of the polypeptide dTCApFs is denoted herein by SEQ ID NO: 1. The polypeptide dTCApFs is the C-terminal 14 all D amino acid fragment of the "full T101 peptide" previously reported.

In other words, the present disclosure relates to use of an isolated polypeptide (interchangeably referred to herein as "peptide", "isolated peptide" or "isolated polypeptide") comprising the amino acid sequence of SEQ ID NO: 1 or a functional fragment or derivative of the isolated polypeptide or a salt thereof.

As known in the art, a "polypeptide" refers to a molecular chain of amino acid residues, which can be optionally modified at one or more of its amino acid residues, for example by manosylation, glycosylation, amidation (for example C-terminal amides), carboxylation or phosphorylation. The polypeptide of the present disclosure may be obtained synthetically, through genetic engineering methods, expression in a host cell, or through any other suitable means as known in the art. Methods for producing peptides or polypeptides are well known in the art.

The terms "amino acid" or "amino acid residue" as used herein, refer to naturally occurring and synthetic amino acid residues, as well as amino acid analogues and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term amino acid encompasses L-amino acids and D-amino acids, which are mirror images of L-amino acids, where the chirality at carbon alpha has been inverted. In particular, the polypeptide dTCApFs according to the present disclosure is an all D amino acid residue polypeptide, as detailed above.

The terms "amino acid sequence" or "polypeptide sequence" also relate to the order in which amino acid residues, connected by peptide bonds, lie in the chain in peptides and proteins. The sequence is generally reported from the N-terminal end containing free amino group to the C-terminal end containing free carboxyl group.

The present disclosure further encompasses any pharmaceutically acceptable salt of said isolated polypeptide or peptide. The term "isolated" refers to molecules, such as the amino acid sequences described herein, peptides or polypeptides that are removed from their natural environment, isolated, or separated.

By the term "comprising" it is meant that the isolated polypeptide in accordance with the present disclosure includes the amino acid sequence denoted by SEQ ID NO: 1, as detailed above, but may also include additional amino acid residues at the N-terminus or at the C-terminus of the peptide or at both termini.

Furthermore in various embodiments the isolated polypeptide according to the present disclosure encompasses a polypeptide comprising the amino acid sequence denoted by SEQ ID NO: 1, in which the N-terminus and/or the C-terminus of the peptide denoted by SEQ ID NO: 1 carries a protecting group. Protective (or protecting) groups are well known in the art and include inter alia alcohol protecting groups, amine protecting groups, carbonyl protecting groups and others.

As indicated above, the present disclosure also encompasses a functional fragment or derivative of the isolated polypeptide as defined herein.

The term "fragment" as herein defined refers to any peptide or polypeptide which is at least one amino acid shorter than the isolated polypeptide in accordance with the present disclosure, obtained by deletion of at least one amino acid residue from the polypeptide in accordance with the present disclosure.

In some embodiments, a fragment of the isolated polypeptide in accordance with the present disclosure is a polypeptide that comprises a contiguous amino acid portion of SEQ ID NO: 1, that is 1, 2, 3, 4, 5 or more amino acid residues shorter than the sequence denoted by SEQ ID NO: 1.

By the term "derivative" or "derivatives" it is meant to include polypeptides, which comprise the amino acid sequence denoted by SEQ ID NO: 1, but differ in one or more amino acid residues in their overall sequence, namely, which have deletions, substitutions (e.g. replacement of at least one amino acid by another amino acid), inversions or additions within the overall sequence. This term also encompasses the replacement of at least one amino acid residue in the overall sequence by its respective L amino acid residue.

Derivatives also encompass amino acid sequence denoted by SEQ ID NO: 1, in which at least one amino acid residue is replaced by a synthetic amino acid residue, an amino acid analogue or an amino acid mimetic.

As known in the art, amino acid "substitutions" are the result of replacing one amino acid with another amino acid, for example with another amino acid that has similar structural and/or chemical properties (conservative amino acid replacements). Amino acid substitutions may be made based on similarity in polarity, charge, solubility, hydrophobicity, hydrophilicity, and/or the amphipathic nature of the residues involved. For example, each of the following eight groups contains amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

It is appreciated that the fragment or derivative of the isolated polypeptide as defined herein must not alter the biological activity of the original polypeptide. By the term "functional" it is meant to encompass any fragment or derivative of the amino acid sequence denoted by SEQ ID NO: 1, which retains a biological activity qualitatively similar to that of the unmodified polypeptide (namely a polypeptide having the amino acid sequence denoted by SEQ ID NO: 1. The biological activity of the fragment or derivative as herein defined may be determined by any method known in the art, for example by monitoring the effect of administering the polypeptide as herein defined to model cells or animals.

In particular embodiments, the present disclosure relates to a functional fragment or derivative of the isolated polypeptide comprising amino acid sequence denoted by SEQ ID NO: 1, wherein said functional fragment or derivative has an amino acid sequence that is at least about 70%, 75%, 80%, 85%, 90%, more preferably 95%, in particular 96%, 97%, 98% or 99% identical to the amino acid sequence of the unmodified isolated polypeptide of the present disclosure, namely to one of the amino acid sequences denoted by SEQ ID NO: 1.

In specific embodiments, the functional fragment or derivative of the polypeptide as herein defined has at least 70% identity to the amino acid sequence denoted by SEQ ID NO. 1. In further specific embodiments, the polypeptide as herein defined consists of the amino acid sequence denoted by SEQ ID NO. 1.

It should be appreciated that the terms "identical", or percent "identity", in the context of two or more amino acids or nucleic acids sequences, refer to two or more sequences that are the same or have a specified percentage of amino acid residues or nucleotides that are the same (i.e., about 70%, identity, 75% identity, preferably 80%, 85%, 90%, or higher identity) over a specified region, when compared and aligned for maximum correspondence over a comparison window.

The peptide of the present disclosure may be administered per se or in combination with another active agent.

Thus in various further embodiments, the method as herein defined further comprises administering at least one additional therapeutic agent to said subject.

By the term "additional therapeutic agent" in the context of the present disclosure it is referred to any therapeutic agent known to a skilled physician for the treatment or prevention of a neurodegenerative disease. For example, Aricept®, Exelon®, Razadyne®, Memantine, Namenda® or Levodopa, to name but few, may be used as additional therapeutic agents for the treatment of the respective neurodegenerative disease as further detailed below.

In some embodiments, the subject suitable for the methods of the present disclosure is not suffering from any type of cancer. In some specific embodiments, the subject is not suffering from brain cancer, e.g. neuroblastoma.

All the embodiments as described above and further below, concerning the uses, compositions and kits of the isolated peptide according to the present disclosure are relevant to all the different aspects disclosed herein.

In a second of its aspects, the present disclosure further provides a method for improving at least one of cognitive function, short term memory, long term memory, learning function, glucose metabolism and glucose transport in a subject in need thereof, comprising administering to said subject an effective amount of an isolated polypeptide comprising the amino acid sequence of SEQ ID NO: 1 or a functional fragment or derivative of the isolated polypeptide or a salt thereof.

In some embodiments the peptide of the present disclosure may be administered in a pharmaceutical composition along with a pharmaceutically acceptable excipient, carrier, or diluent.

Administration of the isolated polypeptide or a functional fragment or derivative thereof or a pharmaceutical composition comprising the same according to the present disclosure may be performed by any one of the acceptable routes, for example but not limited to oral administration, intravenous, intramuscular, intraperitoneal, intrathecal or subcutaneous injection, intra-rectal administration, intranasal administration, ocular administration or topical administration.

As mentioned above, the functional fragment or derivative according to the present disclosure has at least 70% identity to the amino acid sequence denoted by SEQ ID NO. 1.

In some more specific embodiments, the polypeptide consists of the amino acid sequence denoted by SEQ ID NO. 1.

In a further aspect, the present disclosure provides a combination therapy comprising an isolated peptide comprising the amino acid sequence denoted by SEQ ID NO. 1 or a functional derivative thereof or a pharmaceutically acceptable salt of said isolated peptide and at least one additional therapeutic agent for use in a method of preventing, treating, ameliorating or delaying the onset of at least one of a neurodegenerative disease, cognitive decline and any conditions or symptoms associated therewith in a subject in need thereof.

In another aspect, the present disclosure provides a combination therapy comprising an isolated peptide comprising the amino acid sequence denoted by SEQ ID NO. 1 or a functional derivative thereof or a pharmaceutically acceptable salt of said isolated peptide and at least one additional therapeutic agent for use in improving at least one of cognitive function, short term memory, long term memory, learning function, glucose metabolism and glucose transport in a subject in need thereof.

In some embodiments, the at least one additional therapeutic agent may refer to any therapeutic agent known to a skilled physician for the treatment or prevention of Alzheimer's disease.

Although current medications cannot cure Alzheimer's, some treatments address the underlying biology. Other medications may help lessen symptoms, such as memory loss and confusion. To date, the U.S. Food and Drug Administration (FDA) has approved medications that fall into two categories: drugs that may change disease progression in people living with Alzheimer's, and drugs that may temporarily mitigate some symptoms of Alzheimer's disease.

The drugs that may change disease progression may provide benefits to both cognition and function in people living with Alzheimer's disease. For example, Aducanumab (Aduhelm™) is an anti-amyloid antibody intravenous (IV) infusion therapy approved for Alzheimer's disease. In some embodiments, the at least one additional therapeutic agent may be Aducanumab (Aduhelm™).

Among the drugs that treat symptoms, there are some for cognitive symptoms and others for non-cognitive symptoms (memory and thinking).

While medications that treat cognitive symptoms do not stop the damage Alzheimer's causes to brain cells, they may help lessen or stabilize symptoms for a limited time by affecting certain chemicals between the brain's nerve cells.

The following medications are non-limiting examples of drugs prescribed to treat symptoms related to memory and thinking.

In some embodiments, the at least one additional therapeutic agent may be a cholinesterase inhibitor.

Cholinesterase inhibitors are prescribed to treat symptoms related to memory, thinking, language, judgment and other thought processes. These medications prevent the breakdown of acetylcholine, a chemical messenger important for memory and learning. These drugs support communication between nerve cells.

Non-limiting examples of cholinesterase inhibitors suitable according to the present disclosure are: Donepezil (Aricept®) approved to treat all stages of Alzheimer's disease, Rivastigmine (Exelon®) approved for mild-to-moderate Alzheimer's as well as mild-to-moderate dementia associated with Parkinson's disease and Galantamine (Razadyne®) approved for mild-to-moderate stages of Alzheimer's disease.

In some embodiments, the at least one additional therapeutic agent may be a glutamate regulator.

Glutamate regulators are prescribed to improve memory, attention, reason, language and the ability to perform simple tasks. This type of drug works by regulating the activity of glutamate, a different chemical messenger. For example, Memantine (Namenda®) was approved for moderate-to-severe Alzheimer's disease.

Furthermore, an additional exemplary treatment may be a combination of a cholinesterase inhibitor and a glutamate regulator such as Donepezil and memantine (Namzaric®) approved for moderate-to-severe Alzheimer's disease.

An example of medications for treating non-cognitive symptoms of Alzheimer's disease i.e. behavioral and psychological symptoms such as sleep disturbances, agitation, hallucinations and delusions may be an Orexin receptor antagonist. Orexin receptor antagonist such as Suvorexant (Belsomra®) is prescribed to treat insomnia for individuals living with dementia, this drug is thought to inhibit the activity of orexin, a type of neurotransmitter involved in the sleep-wake cycle and is approved for mild-to-moderate Alzheimer's disease.

In some embodiments, the at least one additional therapeutic agent suitable for the combination therapy disclosed herein is any one of cholinesterase inhibitors, glutamate regulators, a combination of a cholinesterase inhibitor and a glutamate regulators, Orexin receptor antagonist or Aducanumab.

In certain embodiments, the isolated peptide and said additional therapeutic agent are administered concomitantly or consecutively.

Still further in an additional aspect, the present disclosure provides an isolated polypeptide comprising the amino acid sequence of SEQ ID NO: 1 or a functional fragment or derivative of said isolated polypeptide or a salt thereof for use in a method for preventing, treating, ameliorating or delaying the onset of at least one of a neurodegenerative disease, cognitive decline and any conditions or symptoms associated therewith in a subject in need thereof, said method comprises administering to said subject an effective amount of said isolated polypeptide, a functional fragment or derivative of said isolated polypeptide or of a salt thereof.

In some embodiments, the isolated polypeptide, functional fragment or derivative or salt thereof for use according to the present disclosure is wherein the method results in amelioration or reduction of at least one condition or symptom associated with at least one of a neurodegenerative disease and cognitive decline in a subject in need thereof.

In other embodiments, the isolated polypeptide, functional fragment or derivative or salt thereof for use according to the present disclosure is wherein the condition or symptom is at least one of anxiety, short term memory impairment, long term memory impairment, impaired cognitive function, impaired learning function, impaired glucose metabolism, oxidative stress or any combination thereof.

In further embodiments the isolated polypeptide, functional fragment or derivative or salt thereof for use according to the present disclosure is wherein the method results in improvement of at least one of cognitive function, short term memory, long term memory, learning function, glucose metabolism and glucose transport in a subject in need thereof.

In some embodiments, the isolated polypeptide according to the present disclosure is for use in a method for preventing or delaying the onset of at least one of a neurodegenerative disease, cognitive decline and any conditions or symptoms associated therewith in a subject in need thereof.

In further embodiments, the isolated polypeptide, functional fragment or derivative or salt thereof for use according to the present disclosure is for preventing, treating, ameliorating, or delaying the onset of cognitive decline.

As mentioned above, the neurodegenerative disease is Alzheimer's disease, Parkinson's disease, Dementia, a disorder associated with protein misfolding, cognitive decline, Mild Cognitive Impairment (MCI), Parkinson's disease with MCI, Huntington's disease, Lewy body disease, Amyotrophic lateral sclerosis (ALS), Prion disease, Motor neuron disease (MND), Spinocerebellar ataxia (SCA), Spinal muscular atrophy (SMA), Friedreich's Ataxia, multiple sclerosis, Idiopathic Intracranial Hypertension, Cranial neuropathies, Trigeminal neuralgia, frontotemporal dementias (FTD), Senile Dementia (Dementia NOS), Motor Neuron Disease, or bipolar disorder.

In various embodiments the isolated polypeptide, functional fragment or derivative or salt thereof for use according to the present disclosure is applicable to Alzheimer's disease, Parkinson's disease, Dementia or cognitive decline.

In some embodiments, neurodegenerative disease is Alzheimer's disease.

In certain embodiments, the isolated polypeptide, functional fragment or derivative or salt thereof for use according to the present disclosure is for preventing, treating, ameliorating, or delaying the onset of cognitive decline.

In some embodiments, the functional fragment or derivative of the isolated peptide as disclosed herein has at least 70% identity to the amino acid sequence denoted by SEQ ID NO. 1.

In certain embodiments, the polypeptide consists of the amino acid sequence denoted by SEQ ID NO. 1.

In some further embodiments, the polypeptide is able to penetrate the Blood Brain Barrier.

As mentioned above, the isolated peptide as disclosed herein is for use in a method that results in protection from oxidative stress in the neurons of said subject.

In some specific embodiments, the isolated peptide modulates the expression of at least one gene associated with protection from oxidative stress.

In certain embodiments, the at least one gene is any one of SOD1, BDNF and TH.

As mentioned above, the isolated peptide as disclosed herein is for use in a method that results in increasing glucose metabolism and/or transport in the neurons of said subject.

In some specific embodiments, the isolated peptide modulates the expression of at least one gene associated with glucose metabolism and/or transport.

In certain embodiments, the at least one gene is any one of GLUT1, GLUT3 and P53.

As mentioned above, the isolated peptide as disclosed herein is for use in a method comprising administering a pharmaceutical composition comprising said isolated polypeptide or a functional fragment or derivative of said isolated peptide or a salt thereof.

In some further embodiments, the isolated peptide as disclosed herein is for use in a method further comprising administering at least one additional therapeutic agent to said subject.

In a further aspect, the present disclosure provides an isolated polypeptide comprising the amino acid sequence of SEQ ID NO: 1 or a functional fragment or derivative of said isolated peptide or a salt thereof for use in a method for improving at least one of cognitive function, short term memory, long term memory, learning function, glucose metabolism and glucose transport in a subject in need thereof, said method comprises administering to said subject an effective amount of said isolated polypeptide, a functional fragment or derivative of said isolated peptide or of a salt thereof.

As mentioned above in some embodiments, the functional fragment or derivative of the isolated peptide as disclosed herein has at least 70% identity to the amino acid sequence denoted by SEQ ID NO. 1. In certain embodiments, the polypeptide consists of the amino acid sequence denoted by SEQ ID NO. 1.

Still further the present disclosure provides a pharmaceutical composition comprising an isolated polypeptide comprising the amino acid sequence of SEQ ID NO: 1 or a functional fragment or derivative of said isolated polypeptide or a salt thereof, and at least one pharmaceutically acceptable excipient, carrier or diluent, for use in a method for preventing, treating, ameliorating or delaying the onset of at least one of a neurodegenerative disease, cognitive decline and any conditions or symptoms associated therewith in a subject in need thereof.

In some embodiments, the pharmaceutical composition comprising the isolated peptide as disclosed herein is use in a method for preventing or delaying the onset of at least one of a neurodegenerative disease, cognitive decline and any conditions or symptoms associated therewith in a subject in need thereof.

By a further aspect thereof the present disclosure provides a pharmaceutical composition comprising an isolated polypeptide comprising the amino acid sequence of SEQ ID NO: 1 or a functional fragment or derivative of said isolated polypeptide or a salt thereof, and at least one pharmaceutically acceptable excipient, carrier or diluent, for use in a method for improving at least one of cognitive function, short term memory, long term memory, learning function, glucose metabolism and glucose transport in a subject in need thereof.

The term "pharmaceutical composition" as herein defined generally comprises as an active agent an isolated polypeptide according to the present disclosure (namely an isolated polypeptide comprising or consisting of the amino acid sequence denoted by SEQ ID NO: 1) or a functional fragment or derivative of the isolated polypeptide or a salt thereof, and at least one of a buffering agent, an agent which adjusts the osmolarity thereof, and optionally, at least one pharmaceutically acceptable excipient, carrier, diluent and/or additive as known in the art.

As used herein the term "pharmaceutically acceptable excipient, carrier, diluent and/or additive" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

The pharmaceutical compositions according to the invention may be prepared according to conventional techniques well known in the pharmaceutical industry. Such techniques include the step of bringing into association the active ingredients with the pharmaceutically acceptable carrier(s), excipient(s) or additive(s).

For example, the term "pharmaceutically acceptable carrier" as used herein includes any and all solvents, dispersion media, coatings, antibacterial and antifungal agents as well known in the art. Each carrier should be both pharmaceutically and physiologically acceptable in the sense of being compatible with the other ingredients and not injurious to the patient.

The pharmaceutically acceptable carrier can be a solvent or dispersion medium containing, for example, water, ethanol, polyol (for example, glycerol, propylene glycol, and liquid polyethylene glycol, and the like), suitable mixtures thereof, and vegetable oils.

Supplementary or additive active ingredients, for example additional anti-cancer agents, can also be incorporated into the pharmaceutical composition of the invention.

It should be understood that in addition to the ingredients particularly mentioned above, the formulations may also include other agents conventional in the art having regard to the type of formulation in question, for example those suitable for oral administration may include flavoring agents.

By the term "effective amount" as used herein it is meant an amount necessary to achieve a desirable result. The effective amount is determined by the severity and type of the disease or condition in conjunction with the preventive or therapeutic objectives, the route of administration and the patient's general condition (age, sex, weight and other considerations known to the attending physician). The effective amount may be determined based on animal models and is determined by a skilled physician.

By the term "subject in need thereof" or "subject" as used herein it is meant to include warm-blooded animals (such as for example humans, rats, mice, dogs, cats, guinea pigs and primates). In particular embodiments, the subject is human.

In some embodiments the subject according to the present disclosure is diagnosed by a skilled physician as being at a risk of developing a neurodegenerative disease or cognitive decline. In some other embodiments the subject is diagnosed as having the disease, disorder or condition as herein defined. Diagnosis of the disease, disorder or condition as herein defined may be performed by a skilled physician, by means and steps as known in the art.

In certain embodiments, the polypeptide of the pharmaceutical composition for use according to the present disclosure consists of the amino acid sequence denoted by SEQ ID NO. 1.

In some particular embodiments, the neurodegenerative disorder is Alzheimer's disease.

In another aspect, the present disclosure further provides a kit comprising:

(a) an isolated polypeptide comprising the amino acid sequence of SEQ ID NO: 1 or a functional fragment or derivative of the isolated polypeptide or a salt thereof; and optionally (b) at least one pharmaceutically acceptable excipient, carrier or diluent;

for use in a method for at least one of preventing, treating, ameliorating or delaying the onset of at least one of a neurodegenerative disease, cognitive decline and any conditions or symptoms associated therewith in a subject in need thereof.

A further aspect of the present disclosure provides a kit comprising:

(a) an isolated polypeptide comprising the amino acid sequence of SEQ ID NO: 1 or a functional fragment or derivative of the isolated polypeptide or a salt thereof; and optionally (b) at least one pharmaceutically acceptable excipient, carrier or diluent;

for use in a method for improving at least one of cognitive function, short term memory, long term memory, learning function, glucose metabolism and glucose transport in a subject in need thereof.

The kit according to the present disclosure may further include instructions for use.

The isolated polypeptide according to the present disclosure or a functional fragment or derivative of the isolated polypeptide or a salt thereof and the at least one pharmaceutically acceptable excipient, carrier or diluent may be contained in the same container or in different ones. Still further, the kit according to the present disclosure may include container means for containing separate kit components. In some embodiments the kit of the present disclosure further includes at least one solvent or buffer known in the art.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprise", "comprises", "comprising", "includes", "including", "having" and their conjugates mean "including but not limited to". This term encompasses the term "consisting of". Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Various embodiments and aspects of the present invention as delineated hereinabove and as claimed in the claims section below find experimental support in the following examples. The following examples are representative of techniques employed by the Inventors in carrying out aspects of the present invention. It should be appreciated that while these techniques are exemplary for the practice of the invention, those of skill in the art, in light of the present disclosure, will recognize that numerous modifications can be made without departing from the spirit and intended scope of the invention.

It must be noted that, as used in this specification and the appended claims, the singular forms "a", "an" and "the" include plural referents unless the content clearly dictates otherwise.

EXAMPLES

Reference is now made to the following examples, which together with the above descriptions illustrate some embodiments of the invention in a non-limiting fashion.

Experimental Procedures

Mice

ICR female mice having initial body weight of 20-22 grams were used (Envigo).

Blood Brain Barrier (BBB) Penetration Assay

A control group of 6 mice was injected intraperitoneally (I.P.) with 5% mannitol solution and another group of 6 mice was injected I.P. with the polypeptide dTCApFs (also termed herein Nerofe, at 60 mg/kg) in a 5% mannitol solution. Spinal fluid was collected after the injection (1 hour) and subjected to ELISA analysis of dTCApFs (Nerofe), as detailed below.

ELISA Analysis of Mice Cerebrospinal Fluids

Mice were injected with 60 mg/kg D-amino acid dTCApFs (Nerofe), and cerebrospinal fluid (about 10 μl) and serum were collected after 1 hr, and frozen. A calibration curve was prepared by serial dilutions of the polypeptide in PBS (Biological industries, 02-023-5A) as noted in table 1 below.

Next, the cerebrospinal samples were thawed and kept on ice, and then diluted in 220 μl PBS. Sample loading was next performed by loading 100 μl duplicates of each sample and of the standard in a Maxisorp 96-wells plate (NUNC, F96 Maxisorp, 442404). The plate was sealed and incubated at 4° C. overnight with gentle shaking. The plate was washed by removing the liquid and washing the plate four (4) times using a multi-pipette or an automated washer with 300 μl 0.05% TW-20 (Amresco, 0777-1L) in PBS. The samples were blocked by diluting 5% BSA (MP biomedicals, 160069) in PBS. Then, 300 μl of the blocking buffer were loaded in each well and the plate was incubated at room temperature (R.T.) for 1 hour with gentle shaking. The Plates were washed again, as described above.

Detection was performed by diluting the first antibody according to table 1 below in diluent (0.05% TW-20, 0.1% BSA in PBS). Then, 100 μl of detection antibody were loaded into each well and the plate was incubated at R.T. for 2:00 hours with gentle shaking. The plate was washed again as detailed above. Next, HRP conjugate was prepared by diluting goat anti-rabbit HRP conjugate antibody (Cell signaling, 7074) according to table 1 in diluent. HRP conjugate (100 μl) was then loaded into each well and the plate was incubated for 1:00 hour at R.T. with gentle shaking. The plate was washed again, as detailed above.

Development was performed by adding 100 μl TMB (Milipore, ES001-500ML) to each well, and waiting for blue color development, then adding 100 μl 2N $H_2SO_4$ (Frutarom, 5552540). Plate reading was performed in a microplate reader, by checking the wells absorbance at 450 nm.

TABLE 1

| Calibration curve preparation | | | |
|---|---|---|---|
| Peptide | Calibration curve range | 1st antibody dilution | Secondary antibody dilution |
| dTCApFs | 1000-15.6 pg/ml | 1:250 | 1:300 |

Preparation of the dTCApFs Peptide and Compositions Comprising Thereof

The polypeptide termed herein dTCApFs (or Nerofe, both terms are used herein interchangeably and refer to the same peptide as indicated above) is a 14 amino acid residues long peptide, in which all of the amino acid residues are at their D configuration, having the amino acid sequence of Trp Trp Thr Phe Phe Leu Pro Ser Thr Leu Trp Glu Arg Lys (or WWTFFLPSTLWERK in a single letter code, as denoted by SEQ ID NO: 1). A peptide having an amino acid sequence of Trp Trp Thr Phe Phe Leu Pro Ser Thr Leu Trp Glu Arg Lys (or WWTFFLPSTLWERK in a single letter code, as denoted by SEQ ID NO: 2) in which all of the amino acid residues are at their L configuration, was also used. The above D-amino acid peptide was GMP manufactured in BCN peptides at Barcelona. The above L-amino acid peptide was manufactured at Anaspec Inc., in the USA.

Cell Viability Assay (Resazurin) of Cells Treated with dTCApFs (Nerofe)

Materials:

Clear bottom 96 well cell culture plates (Greiner 60-65590)

Cell Culture Media:

10% FBS (Biological industries, cat #04-121-1A)

RPMI (Gibco cat #21875034)

100 u/ml penicillin and 100 μg/ml streptomycin (Biological Industries)

250 ng/ml Amphotericin B (Biological Industries)

Cell Treatment Media: Cell Culture media +5% Mannitol (Filter after Mannitol addition)

Cell Cytotoxicity Assay Kit (Colorimetric): ab112118 abcam

Cell Line

SH-SY5Y (ATCC® CRL-2266™)

For Treatment:

2 mg/ml dTCApFs (Nerofe) stock solution: Dilute 100 μl of 20 mg/ml dTCApFs (Nerofe) in 900 μl Cell treatment media 4μ8C (sigma SML0949)

Cyclic Pifithrin-α hydrobromide (sigma P4236)

TABLE 2

| Treatment regime | | | |
|---|---|---|---|
| 4u8C 4 hours before dTCApFs (mM) | Cyclic Pifithrin-α hydrobromide 4 hours before dTCApFs (mM) | dTCApFs 24 hours (mg/ml) | mM $H_2O_2$ 24 hours |
| 0 | 0 | 0 | 0 |
| 5 | 0 | 0.1 | 0.025 |

TABLE 2-continued

| Treatment regime | | | |
|---|---|---|---|
| 4u8C 4 hours before dTCApFs (mM) | Cyclic Pifithrin-α hydrobromide 4 hours before dTCApFs (mM) | dTCApFs 24 hours (mg/ml) | mM $H_2O_2$ 24 hours |
| 5 | 0 | 0.5 | 0.025 |
| 5 | 0 | 1 | 0.025 |
| 0 | 10 | 0.1 | 0.025 |
| 0 | 10 | 0.5 | 0.025 |
| 0 | 10 | 1 | 0.025 |
| 5 | 0 | 0 | 0.025 |
| 0 | 10 | 0 | 0.025 |
| 5 | 0 | 0 | 0 |
| 0 | 10 | 0 | 0 |
| 0 | 0 | 0 no cells | 0.025 no cells |

Procedure

The cells were seeded at 5,000 cells/well in a black 96 well plate with clear bottom, in 100 ml growing media. All unused wells were filled with 100 ml media. The cells were incubated for 24 hours. Next, the media was removed, and the cells were first treated with inhibitors (namely 4u8c and Cyclic Pifithrin-α hydrobromide) in 50 ml treatment media. The cells were then incubated for four (4) hours. The cells were next treated with dTCApFs (Nerofe) by adding 50 ml treatment media with dTCApFs (a ×2 dTCApFs stock was prepared and added appropriately to each well). Control wells were filled with 50 ml treatment media. The cells were incubated for 24 hours. Then the media was removed and 100 ml $H_2O_2$ were added to each well in growing media. Next, 100 ml growing media were added to the control wells. The cells were incubated for 24 hours.

Finally, 20 ml of Cell Cytotoxicity Assay Kit (Colorimetric) ab112118 were added to each well, and the cells were incubated for 4 hours. The cells were read at excitation 530 and emission 590, sensitivity 40, using Biotek Synergy-HT plate reader. The results were calculated as follows: the percentage of cells viability compared to control was calculated.

Expression of the Proteins Glut1, XBP1 and p53 in Human Neuroblastoma Cells

The expression levels of XBP1, p53 and Glut1 were examined by Western blot of SHSY5Y cells treated with dTCApFs (the all D-amino acid residue polypeptide) and the corresponding L-amino acid residue polypeptide.

Materials for Cell Growth:

- Growing Medium—
  - DMEM high glucose, L-Glutamine (Gibco 41965-039)
  - Sodium Pyruvate 11.0 mg/ml (100 mM) (Biological industries cat No. 03-042-1B)
  - 50 ml FBS (Biological industries cat no. 04-121-1A).
  - 0.5 ml Amphotericin B 2500 μg/ml (Biological industries cat no. 03-029-1).
  - Penicillin-Streptomycin Solution (Biological Industries cat no. 03-031)
- Treatment Medium—
  - Growing Medium
  - 5% Mannitol (Sigma cat no. M4125-500G)
    - The media is filtered in 0.2 μm filter after adding Mannitol.
- Trypsin EDTA (Biological industries cat no. 03-052-1B).
- 175 $cm^2$ culture Flasks
- 20 mg/ml all D-amino acid residue dTCApFs (Nerofe) or the corresponding all L-amino acid residue polypeptide in Mannitol (aliquots are used, avoid repeated freeze-thaw cycle).

SHSY5Y cells line

Materials for Western Blot Analysis:

Lysis Buffer containing:

Ripa Buffer (Sigma R0278)

Protease inhibitor (Halt™ Protease Inhibitor Cocktail, PIR-78410).

phosphatase inhibitors (Sigma P5726)

Benzonase® Nuclease, Purity >90% (70746 Millipore) 25 U/ml

X4 LDS sample buffer (invitrogen cat #NP0007)

Sample reducing agent (Invitrogen cat #NP0009, 10-fold concentrated)

4-20% Tris-Glycin gel (NuSep cat #NG21-420)

10× TRIS/GLYCINE transfer BUFFER (Bio-Rad 1610734)

PVDF membrane (immobilon-P 0.45 um)

TBST buffer: TBS (J640 Amersco)+0.05% Tween-20

5% skim milk in TBST

1$^{st}$ antibodies diluted in 5% skim milk in TBST:

Anti-XBP1 antibody (ab220783) diluted 1:1,000

Anti-P53 antibody (ab28) diluted 1:1,000

Anti-Glut1 antibody (ab115730) diluted 1:10,000

Secondary antibodies diluted 1:10,000 in 5% skim milk in TBST:

Anti-mouse IgG, HRP-linked Antibody #7076 (Cells signaling)

Anti-rabbit IgG, HRP-linked Antibody #7074 (Cells signaling)

SuperSignal™ West Femto Maximum Sensitivity Substrate (Thermo Scientific 34095)

Cell Culture—Passages:

Cells were grown in an incubator at 37° C., 5% $CO_2$ 100% humidity until reaching 70-80% density on the flask (and not more). The flask was emptied using a pipette. Then Trypsin EDTA were added and the flask was left in the incubator until most of the cells were observed to be not attached to the flask (while avoiding tapping on the flask to increase detaching of the cells), this procedure takes a few minutes. Then 10 ml medium were added to the Trypsin and the medium and Trypsin were divided into 2 flasks, to which 15 ml fresh medium were added. The cells were left to grow 2-3 days until reaching 70-80% and the passage procedure was repeated.

Cells Treatment:

The cells were grown until reaching 70-80% density on the flask (and not more). The cells were detached from the flask by following the Trypsin EDTA procedure detailed above. The cells in medium and Trypsin were transferred into 50 ml conical tube and centrifuged at 300 g for 10 min in 4° C. The supernatant was discarded and 15 ml fresh medium were added to the cells pellet, fluidizing the pellet. Cells were then counted, seeded at 1.5 M cells/75 CM2 flask in 30 ml growing media. The cells were incubated overnight.

The following day, cell treatment medium was prepared as follows (medium including 5% mannitol):

Control

20 μg/ml all D-amino acid residue dTCApFs (SEQ ID NO: 1)

30 μg/ml all D-amino acid residue dTCApFs (SEQ ID NO: 1)

40 μg/ml all D-amino acid residue dTCApFs (SEQ ID NO: 1)

50 μg/ml all D-amino acid residue dTCApFs (SEQ ID NO: 1)

20 μg/ml all L-amino acid residue polypeptide corresponding to dTCApFs (SEQ ID NO: 2)

30 μg/ml all L-amino acid residue polypeptide corresponding to dTCApFs (SEQ ID NO: 2)

40 μg/ml all L-amino acid residue polypeptide corresponding to dTCApFs (acid residue polypeptide corresponding to dTCApFs)

50 μug/ml all L-amino acid residue polypeptide corresponding to dTCApFs (SEQ ID NO: 2)

The media was aspirated from the flasks, and 30 ml of each treatment was added to the corresponding flask. The cells were then incubated for 48 hours and then collected for Western Blot analysis, as detailed below.

Western Blot Analysis Procedure:

Media was discarded and the cells were washed twice with PBS. PBS (5 ml) was added to each flask, the cells were scraped with a cell scraper, and collected into a 15 ml conical tube, which was centrifuged 10 minutes at 300 G, 4° C. The supernatant was then discarded and 90-200 ml lysis buffer was added to the cell pellet, the mixture was pipetted up and down, and incubated 20 minutes on ice. The lysed cells were then centrifuged 15K G for 15 minutes at 4° C., and the supernatant was collected.

Reducing agent was added to each sample, then running buffer (×4 LDS) was added to each sample and the sample was boiled for 5 minutes, vortexed, centrifuged (for Glut1, the sample was not boiled). Next, 30-50 ml of the sample was loaded onto 4-20% Tris Glycin gel and the gel was transferred using semi-dry wet transfer device with rapid transfer buffer onto PVDF membrane 20-60 minutes at 20V. The membrane was blocked for 1 hour with 5% skim milk in TBST with shaking. Then the first antibody was added, for an over-night incubation period at 4° C. with shaking. The membrane was washed three (3) times with TBST and a secondary antibody was added, for an incubation period of 1 hour at room temperature (R.T.) with shaking. Development was performed with an ECL substrate, 5 minutes at R.T. with shaking and the reading was performed using a Lycor C-Digit digital reader.

Example 1

Blood Brain Barrier (BBB) Penetration Ability of dTCApFs in Mice

In order to study the effect of the polypeptide dTCApFs (having the amino acid sequence denoted by SEQ ID NO: 1, also termed herein Nerofe) on brain function, the blood brain barrier (BBB) penetration ability of the polypeptide was examined in mice.

Therefore, a control group of mice was injected intraperitoneally (I.P.) with 5% mannitol solution and another group of mice was injected I.P. with the polypeptide dTCApFs (at 60 mg/kg) in 5% mannitol solution and the spinal fluid of the tested mice was then collected and subjected to analysis, as detailed above.

As shown in FIG. 1A, right bar, the level of dTCApFs in mice brain was dramatically increased following dTCApFs injection, as compared to the level of dTCApFs in the control group (mice injected with 5% mannitol solution, left bar).

The above results show that dTCApFs has a good penetration ability of the BBB in mice.

Figure 1B:
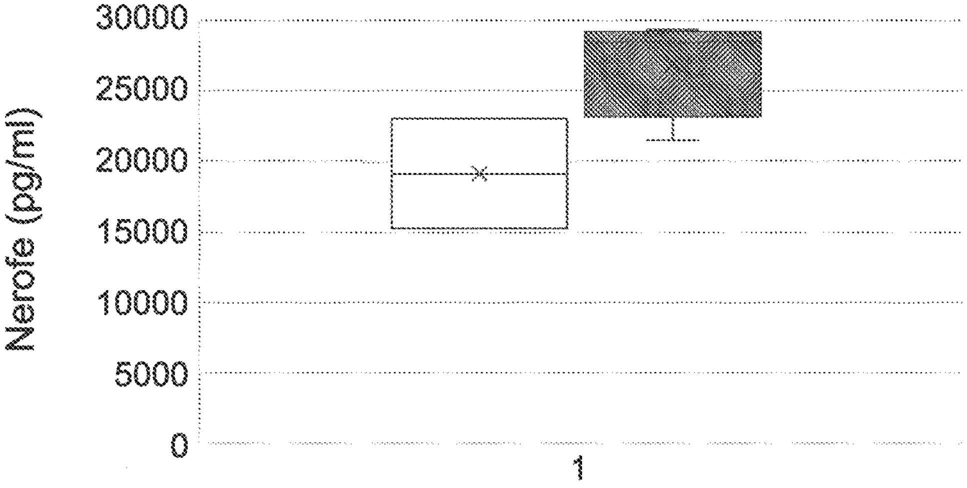

Further to the above experiment and in comparison thereto, the above experiment was performed by injection to mice of a polypeptide having the same amino acid sequence as that of dTCApFs, in which all of the amino acid residues are in their L configuration (as denoted herein by SEQ ID NO: 2). The results presented in FIG. 1B show that this polypeptide is naturally present in mice brain (as judged by the level of the polypeptide in the left bar of FIG. 1B) and therefore the level thereof was changed insignificantly upon injection.

Example 2

The Effect of dTCApFs on Human Neurons in the Presence of Oxidative Stress

SH-SY5Y is a human derived cell line first isolated from a bone marrow biopsy taken from a four-year-old female with neuroblastoma. SH-SY5Y cells are often used as an in vitro model of neuronal function and differentiation, for example to study Parkinson's disease and other characteristics of brain cells.

Using human SH-SY5Y cells model, dTCApFs was shown to protect human neurons from hydrogen peroxide ($H_2O_2$) insults, in a dose dependent manner, as detailed below.

Figure 2:
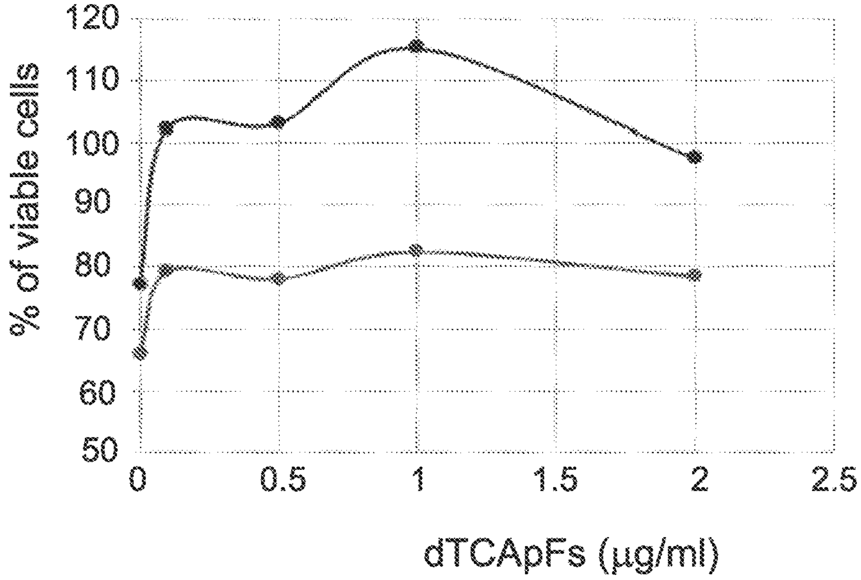
FIG. 2 is a graph showing the percentage of viable cells upon $H_2O_2$ insult at a concentration of 0.1 μM (lower graph) and at a concentration of 0.01 μM (higher graph) in cells incubated in the presence of dTCApFs at the indicated concentrations (μg/ml).

To this end, SH-SY5Y cells were treated with $H_2O_2$ in absence or in the presence of increasing doses of dTCApFs (at 0, 0.5, 1, 1.5 and 2 μg/ml) for 24 hours. Cell viability was measured using the Resazurin reagent, as detailed above. The upper graph in FIG. 2 relates to SH-SY5Y cells treated with 0.01 μM $H_2O_2$ in the presence of increasing doses of dTCApFs. The lower graph in FIG. 2 relates to SH-SY5Y cells treated with a higher concentration of $H_2O_2$ (0.1 μM) in presence of increasing doses of dTCApFs. As can be seen in FIG. 2, at the absence of dTCApFs, the level of cell viability was low in cells treated with two different doses of $H_2O_2$ (namely about 65% in cells treated with 0.1 μM $H_2O_2$ and about 75% in cells treated with 0.01 μM $H_2O_2$). Surprisingly, increasing doses of dTCApFs increased viability of cells in a dose depended manner, in both tested doses of $H_2O_2$.

Example 3

The Effect of dTCApFs on Gene Expression in Human Neurons (SH-SY5Y Cells)

Without wishing to be bound by theory, the above results may indicate that dTCApFs has a protective effect on human neurons from oxidative stress, by inducing the expression of SOD1. Therefore, the mechanism by which SH-SY5Y cells become resistant to oxidative stress in the presence of dTCApFs was next examined.

Using reverse-transcription polymerase chain reaction (RT-PCR), the levels of different genes that may be associated with protection against oxidative stress were determined. Among the genes tested were SOD1, Catalase and others, as detailed below.

SOD1 (Superoxide dismutase also known as superoxide dismutase 1) is an enzyme that in humans is encoded by the SOD1 gene. SOD1 is implicated in apoptosis and familial amyotrophic lateral sclerosis. As known in the art, SOD1 is reactive oxygen species release during oxidative stress.

The gene expression level assay was performed as detailed above. Briefly, SH-SY5Y cells were incubated in the presence of increasing doses of dTCApFs (namely 0, 0.5, 1, 1.5 and 2 μg/ml) and after 24 hours of incubation, cells were harvested and subjected to RT-PCR analysis, directed to different genes, among which were: human beta-actin, BDNF (brain-derived neurotrophic factor, middle graph in FIG. 3), SOD1 (Superoxide dismutase, upper graph in FIG. 3), CATALASE (not shown) and tyrosine hydroxylase (TH, bottom graph in FIG. 3). The induction of the different genes was calibrated against the level of expression of human beta-actin.

BDNF (brain-derived neurotrophic factor, or abrineurin) is a protein that in humans, is encoded by the BDNF gene. BDNF is a member of the neurotrophin family of growth factors, which are related to the canonical nerve growth factor. Neurotrophic factors are found in the brain and the periphery.

Figure 3:
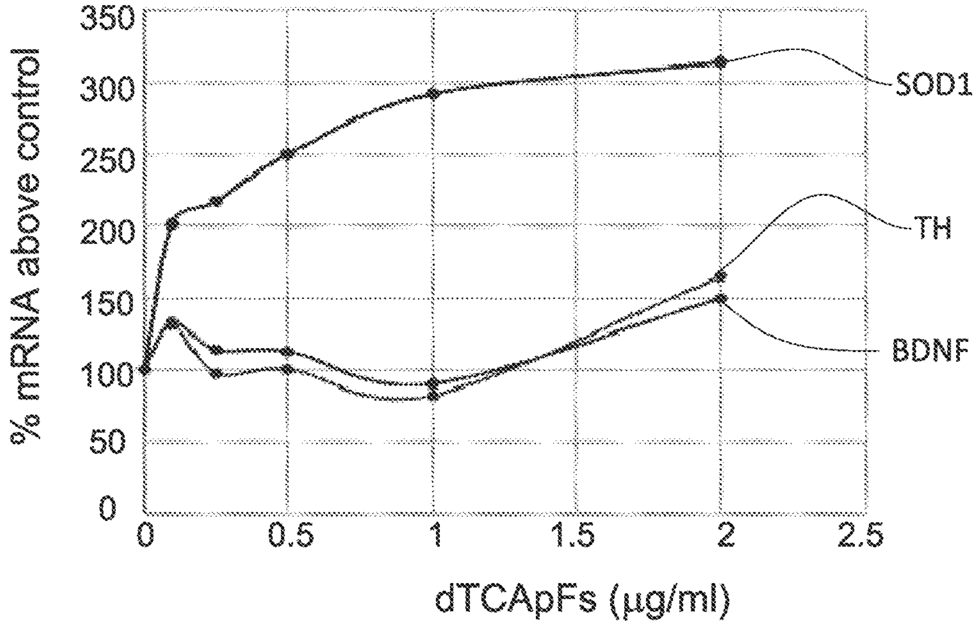
FIG. 3 is a graph showing expression of various genes in SH-SY5Y cells incubated in the presence of the indicated concentrations of dTCApFs (μg/ml).

As shown in FIG. 3, SOD1 was strongly induced by dTCApFs, in a dose dependent manner. BDNF and TH were slightly induced, at some dTCApFs levels. These results indicate that dTCApFs induced a protective effect to the cells, for example via up regulating the expression of SOD1, which assists in cell protection against oxidative stress which is one of the manifestations of the development of neurodegenerative diseases and disorders.

Example 4

The Effect of dTCApFs on Glucose Transporters in Human Neurons

Similar to the other organs in the body, the brain is dependent on glucose as an energy source and requires the expression of glucose transporter proteins to enable passage of glucose across the blood-brain barrier and the plasma membranes of nerve cells. At least two isoforms of glucose transporters which participate in neuronal glucose transport, are known, namely GLUT1 and GLUT3.

Figure 4:
FIG. 4 is a representative micrograph of a Western blot assay showing the expression level of Glut3 and Glut1 in SHSY5Y cells under the indicated conditions (dTCApFs concentration, μg/ml).

In order to study the effect of the polypeptide dTCApFs on the expression level of the above glucose transporters (GLUT1 and GLUT3), SH-SY5Y cells were incubated in the presence of increasing doses of dTCApFs (namely 1, 5 and 10 μg/ml) and after 24 hours of incubation, the cells were harvested, and equal amounts of total protein amounts of the different samples were subjected to Western blot analysis. The expression level of various proteins was monitored, among which were human beta-actin, Glut1 and Glut3. As shown in FIG. 4, the levels of Glut1 and Glu3 proteins were increased with the increase in dTCApFs doses.

It has been previously postulated that oxidative damage is among the key components to the etiology of neurodegenerative diseases. In various neurodegenerative conditions, for example Alzheimer's disease and amnestic mild cognitive impairment, glucose metabolism is dramatically decreased, probably owing, at least in part, to oxidative damage to enzymes involved in glucose metabolism. Consequently, processes required for cognitive function are impaired, and synaptic dysfunction and neuronal death result.

In view of the above results, which demonstrate that incubation of SH-SY5Y cells in the presence of dTCApFs induced expression of the Glut1 and Glut3 proteins, a further beneficial protective effect of the polypeptide on brain function is suggested.

Without wishing to be bound by theory, the effect of dTCApFs observed above suggests that a protective and therapeutic effect on the brain via lowering oxidative stress and positively affecting glucose metabolism.

In other words, in-vitro studies performed with human SH-SY5Y cells shows that the polypeptide dTCApFs protects cells from oxidative stress and increases glucose uptake. Furthermore, in-vitro experiments performed with human microglial cells show that dTCApFs (Nerofe) can downregulate secretion levels of proinflammatory cytokines, such as IL-6, TNFα and soluble ST2 (data not shown).

Example 5

Comparing the Effect of dTCApFs and a Polypeptide Having the Same Amino Acid Sequence in all L Configuration on Protein Expression in Human Neurons As detailed above, human neuroblastoma cells (SH-SY5Y cells), are considered to be an acceptable in vitro model for Alzheimer's disease (AD). In order to examine the effect on these cells of the dTCApFs polypeptide (having the amino acid sequence denoted herein by SEQ ID NO: 1) and in parallel of the polypeptide having the amino acid sequence of dTCApFs in the all L amino acid configuration (having the amino acid sequence denoted herein by SEQ ID NO: 2), SH-SY5Y cells were incubated in the presence of each one the above polypeptide, as detailed above.

Specifically, the effect of the above polypeptides on the expression levels of the proteins Glucose Transporter 1 (GLUT1), X-Box Binding Protein 1 (XBP1) and Tumor protein P53 (P53) in these cells was tested.

As detailed above, the protein Glut1 is an important glucose transporter in the human brain. XBP1 (X-box binding protein 1) in a very important transcription factor in human brain that is involved with increasing memory and cognitive capabilities and p53 in a negative regulator of glucose metabolism in the brain and is highly expressed in Synculin plaques.

Figure 5A:
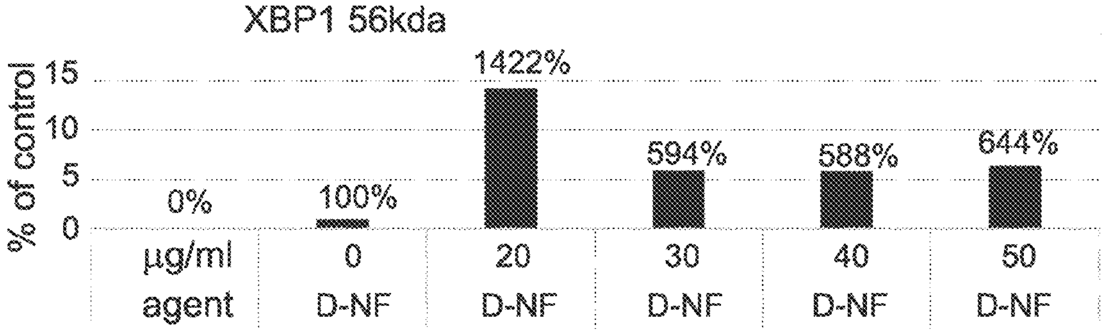
FIG. 5A-FIG. 5C show the effect of dTCApFs (indicated "D-NF") on the expression levels of the proteins XBP1 (FIG. 5A), p53 (FIG. 5B) and GLUT1 (FIG. 5C) in human neuroblastoma cells cells (SHSY5Y cells).
Figure 5B:
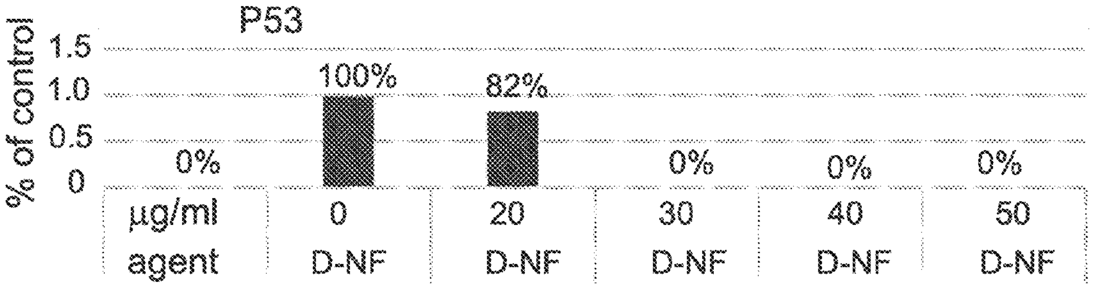
Figure 5C:
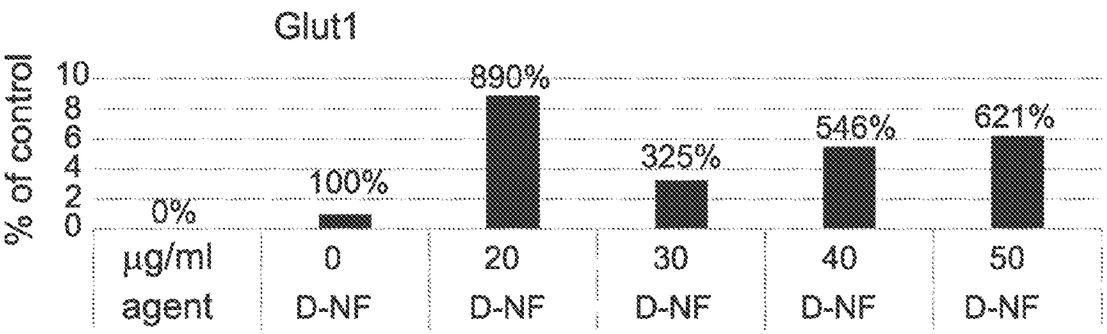
Figure 6A:
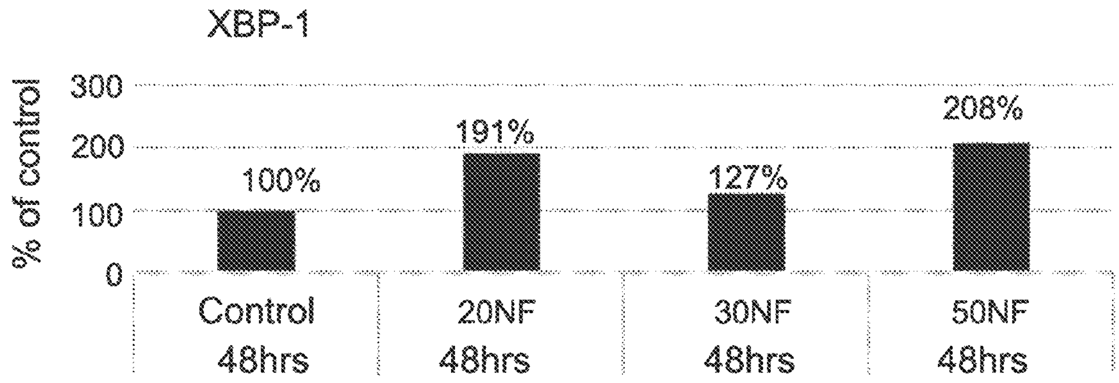
Figure 6B:
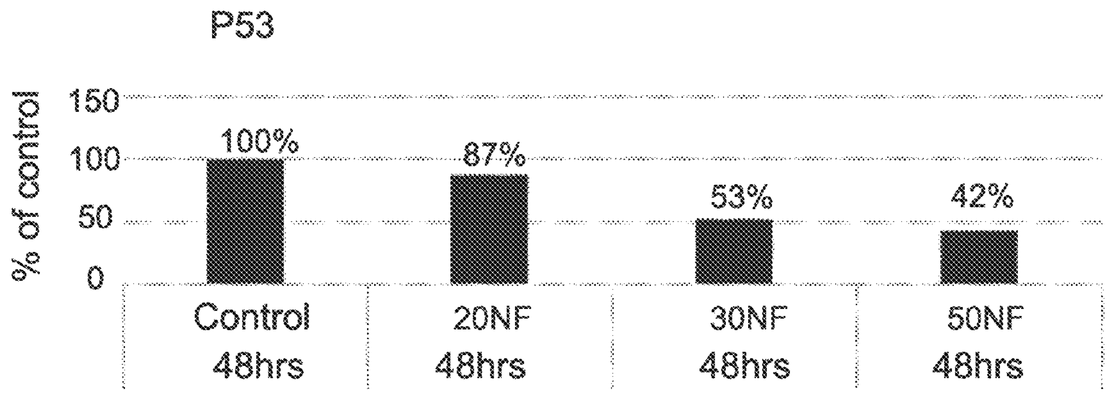
Figure 6C:
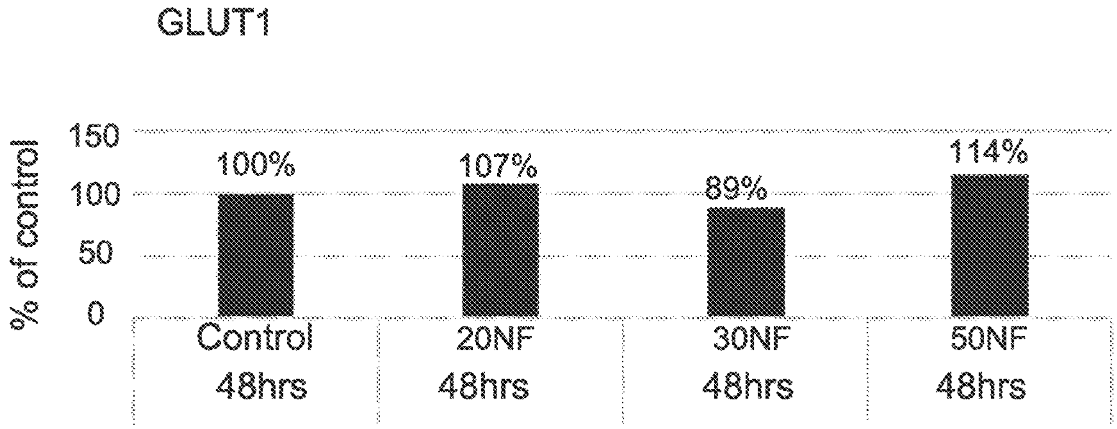

As demonstrated in FIG. 5C, the all D-amino acid dTCApFs (Nerofe) polypeptide was highly efficient in increasing the expression level of the protein Glut1 (about 3-9 fold, as shown in FIG. 5C), as opposed to almost no effect on the expression level of this protein in the presence of the L-amino acid polypeptide (shown in FIG. 6C).

As detailed above, XBP1 is an important transcription factor in human brain to which a beneficial effect on memory and cognitive capabilities is attributed. As shown in FIG. 5A, expression of the protein XBP1 was highly induced in the presence of the dTCApFs polypeptide (for example about 6-fold in the presence of 50 μg/ml dTCApFs and up to 14-fold in the presence of 20 μg/ml dTCApFs as opposed to a rather mild effect on the expression level of this protein in the presence of the L-amino acid polypeptide (about 2-fold in the presence of 20 or 50 μg/ml polypeptide, as shown in FIG. 6A).

Furthermore, incubation of the above cells in the presence of the dTCApFs polypeptide completely downregulated p53 expression in these cells, in a concentration dependent manner (FIG. 5B) as opposed to a modest down regulation observed in the presence of the all L-amino acid polypeptide (FIG. 6B). Lowering the expression level of p53 is considered to be a beneficial effect, since it leads to an increase in glucose metabolism.

Example 6

Comparing the Effect of dTCApFs and a Polypeptide Having the Same Amino Acid Sequence in all L Configuration in the Presence of Oxidative Stress Using human SH-SY5Y cells model, dTCApFs was shown to protect human neurons from hydrogen peroxide ($H_2O_2$) insults better than L-amino acid CTApFs, in a dose dependent manner, as detailed below.

Figure 7:
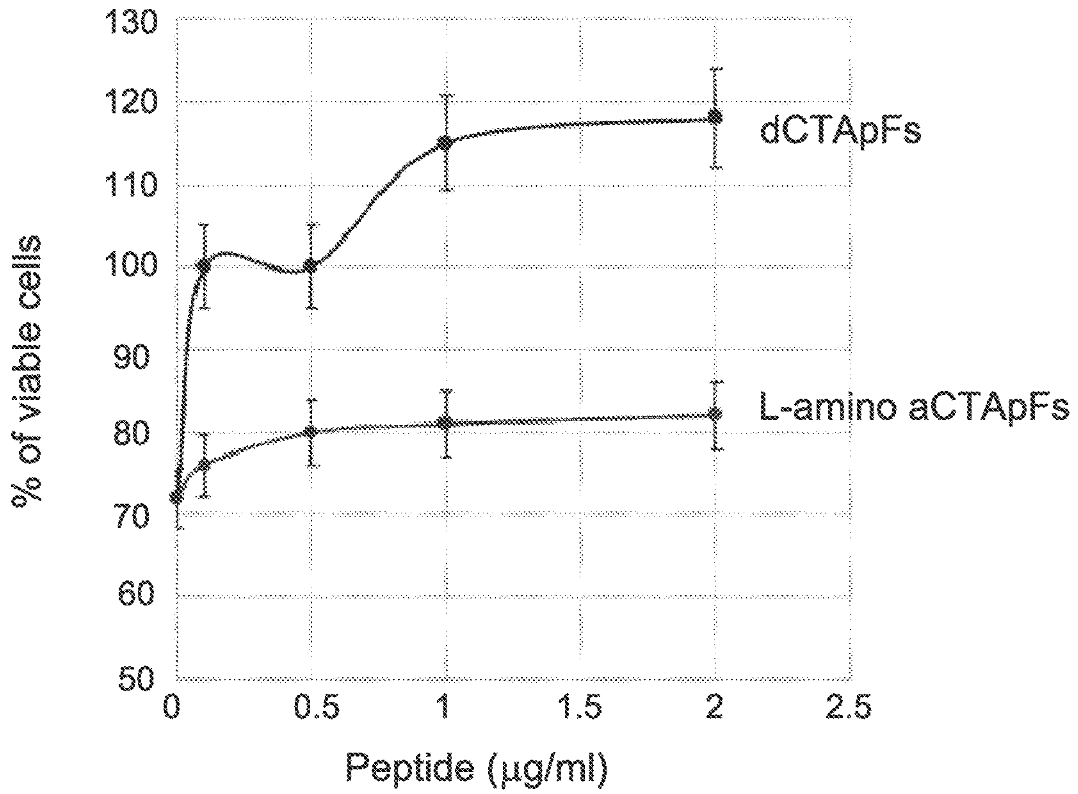
FIG. 7 is a graph showing the percentage of viable cells upon $H_2O_2$ insult at a concentration of 0.1 mM in cells incubated in the presence of dTCApFs (upper graph) or L-amino aCTApFs (lower graph) at the indicated concentrations (μg/ml).

To this end, SH-SY5Y cells were treated with $H_2O_2$ in absence or in the presence of increasing doses of dTCApFs or L-amino acid CTApFs (at 0, 0.5, 1, 1.5 and 2 μg/ml) for 24 hours. Cell viability was measured using the Resazurin reagent, as detailed above. The graph in FIG. 7 relates to SH-SY5Y cells treated with 0.1 mM $H_2O_2$ in the presence of increasing doses of dTCApFs or L-amino acid CTApFs. As can be seen in FIG. 7, when using L-amino acid CTApFs, the level of cell viability was lower than in cells treated with dTCApFs.

These results provide a further example for a beneficial protective and therapeutic cognitive effect for the dTCApFs polypeptide, via the involvement of the affected proteins in various cellular pathways relating thereto.

The invention claimed is:

1. A method for treating or ameliorating at least one of Alzheimer's disease, Parkinson's disease, cognitive decline and any conditions or symptoms associated therewith in a subject in need thereof, the method comprising administering to said subject an effective amount of an isolated polypeptide comprising the amino acid sequence of SEQ ID NO: 1 or a functional fragment or derivative of the isolated polypeptide or a salt thereof, wherein said functional fragment or derivative has at least 90% identity to the amino acid sequence denoted by SEQ ID NO. 1.

2. The method according to claim 1, wherein said method results in amelioration or reduction of at least one condition or symptom associated with Alzheimer's disease, Parkinson's disease and cognitive decline in a subject in need thereof.

3. The method according to claim 2, wherein said condition or symptom is at least one of anxiety, short term memory impairment, long term memory impairment, impaired cognitive function, impaired learning function, impaired glucose metabolism, oxidative stress or any combination thereof.

4. The method according to claim 1, wherein said method results in improvement of at least one of cognitive function, short term memory, long term memory, learning function and glucose metabolism and glucose transport in a subject in need thereof.

5. The method according to claim 1, wherein the method is for treating or ameliorating Alzheimer's disease.

6. The method according to claim 1, wherein the method is for treating or ameliorating cognitive decline.

7. The method according to claim 1, wherein said polypeptide is able to penetrate the Blood Brain Barrier.

8. The method according to claim 1, wherein said method results in protection from oxidative stress in the neurons of said subject and/or wherein said method results in increasing glucose metabolism and/or transport in the neurons of said subject.

9. The method according to claim 1, wherein said peptide modulates the expression of at least one gene associated with protection from oxidative stress, optionally said at least one gene is any one of Superoxide dismutase 1 (SOD1), Brain-Derived Neurotrophic Factor (BDNF) and Tyrosine Hydroxylase (TH).

10. The method according to claim 1, wherein said peptide modulates the expression of at least one gene associated with glucose metabolism and/or transport, optionally wherein said at least one gene is any one of Glucose Transporter 1 (GLUT1), Glucose Transporter 3 (GLUT3) and Tumor protein P53 (P53).

11. The method according to claim 1, wherein said method comprises administering a pharmaceutical composition comprising said isolated polypeptide or a functional fragment or derivative of said isolated polypeptide or a salt thereof.

12. The method according to claim 1, wherein said method further comprises administering at least one additional therapeutic agent to said subject.

13. The method according to claim 12, wherein said at least one additional therapeutic agent is any one of cholinesterase inhibitors, glutamate regulators, a combination of a cholinesterase inhibitor and a glutamate regulators, Orexin receptor antagonist or Aducanumab.

14. The method according to claim 12, wherein said isolated peptide, functional fragment or derivative, or salt, and said additional therapeutic agent are administered to a subject in need concomitantly or consecutively.

15. The method according to claim 1, comprising administering to said subject in need an effective amount of an isolated polypeptide comprising the amino acid sequence of SEQ ID NO: 1 or a salt thereof.

16. The method according to claim 15, for treating or ameliorating Alzheimer's disease.

* * * * *